United States Patent
Nakazawa

(10) Patent No.: US 11,874,137 B1
(45) Date of Patent: Jan. 16, 2024

(54) MEASUREMENT APPARATUS

(71) Applicant: SYNCA GROUP, LTD., Tokyo (JP)

(72) Inventor: Hideta Nakazawa, Tokyo (JP)

(73) Assignee: SYNCA GROUP, LTD., Tokyo (JP)

( * ) Notice: Subject to any disclaimer, the term of this patent is extended or adjusted under 35 U.S.C. 154(b) by 0 days.

(21) Appl. No.: 18/227,941

(22) Filed: Jul. 30, 2023

(30) Foreign Application Priority Data

Nov. 8, 2022 (JP) ................. 2022-178597

(51) Int. Cl.
*G01D 11/24* (2006.01)
*G01N 33/18* (2006.01)
*G01N 27/416* (2006.01)
*A01G 31/02* (2006.01)

(52) U.S. Cl.
CPC ....... *G01D 11/245* (2013.01); *G01N 27/4167* (2013.01); *G01N 33/1886* (2013.01); *A01G 31/02* (2013.01)

(58) Field of Classification Search
CPC ............ G01D 11/245; G01N 27/4167; G01N 33/1886; A01G 31/02
See application file for complete search history.

(56) References Cited

U.S. PATENT DOCUMENTS

| | | | | |
|---|---|---|---|---|
| 3,893,470 A | * | 7/1975 | MacPhee | G05D 11/035 137/101.31 |
| 2022/0406157 A1 | * | 12/2022 | Weeres | G08B 5/38 |

FOREIGN PATENT DOCUMENTS

| | | | |
|---|---|---|---|
| JP | S58-208655 | | 12/1983 |
| JP | S63-157655 | | 6/1988 |
| JP | 2008-133058 | | 6/2008 |
| JP | 2008203174 A | * | 9/2008 |
| JP | 2008-232711 | | 10/2008 |
| JP | 2013-233139 | | 11/2013 |
| JP | 2015216975 A | * | 12/2015 |

OTHER PUBLICATIONS

JPS58208655A—translate (Year: 1982).*
JP-2015216975-A—translate (Year: 2015).*
JP-2008203174-A—translate (Year: 2008).*
JPO, Notice of Allowance in corresponding JP Application 2022-178597, dated Feb. 21, 2023.

* cited by examiner

*Primary Examiner* — Kristina M Deherrera
*Assistant Examiner* — Fatemeh Esfandiari Nia
(74) *Attorney, Agent, or Firm* — Ryan Alley IP

(57) ABSTRACT

A measurement apparatus includes a base having a top portion forming a fulcrum, and a rod-shaped body having a supported portion supported by the top portion, a pH sensor provided on one side thereof, and a reservoir provided on the other side thereof opposite to the one side with the supported portion therebetween, the reservoir being configured to store a fluid. When the reservoir is filled with the fluid, the rod-shaped body is balanced horizontally. When the reservoir is not filled with the fluid, the rod-shaped body is tilted to the side where the pH sensor is provided, so that the pH sensor is immersed in the solution in a water tank.

6 Claims, 5 Drawing Sheets

MEASUREMENT APPARATUS

RELATED APPLICATIONS

This application claims benefit under 35 U.S.C. § 119 of Japanese Application 2022-178597, filed Nov. 8, 2022, which is incorporated by reference herein in its entirety.

FIELD

The embodiment discussed herein relates to a measurement apparatus.

BACKGROUND

Methods for preventing foreign substances from sticking to an object and methods of removing foreign substances from an object are known. For example, there is known a dust adhesion prevention apparatus for preventing dust from sticking to a protective lens that is provided to cover a surface of a sensor that functions to send and receive a detection signal and that is used under the environment where the dust is present. The dust adhesion prevention apparatus includes a cover member which covers the protective lens and in which a gas flow path is formed, and a gas supply unit that supplies gas into the cover member. The cover member includes a gas introduction part which is located away from the protective lens and through which the gas is introduced from the gas supply unit, a gas diffusion part that diffuses the introduced gas in a direction toward the protective lens, and a gas discharge part which is located at a position corresponding to the protective lens and which discharges the gas coming from the gas diffusion part in a direction away from the protective lens. The gas diffusion unit has a rectangular shape. See, for example, Japanese Laid-open Patent Publication No. 2018-103174. In addition, there is known a method of moving horizontally, lifting, and lowering, along a glass surface of a building, a lifting body equipped with a glass surface detection sensor, a glass surface cleaning device, and a photocatalytic film forming device in order to detect the position and size of the glass surface of the building with the glass surface detection sensor, and then cleaning the glass surface with the glass surface cleaning device and forming a photocatalytic film on the glass surface with the photocatalytic film forming device. See, for example, Japanese Laid-open Patent Publication No. 2000-254043.

Hydroponics have become increasingly popular. pH sensors for measuring the pH of an aqueous solution used in the hydroponics are known. For example, if a pH sensor whose surface is covered with a glass film is kept immersed in an aqueous solution, dust sticks to the glass film. To prevent this, it is preferable to immerse the pH sensor in the aqueous solution during measurement periods and not to immerse the pH sensor in the aqueous solution during non-measurement periods. Such measurement is usually carried out manually.

However, there arises a problem that the manual measurement is burdensome.

SUMMARY

According to one aspect, there is provided a measurement apparatus including: a first base having a first supporting portion forming a first fulcrum; and a first rod-shaped body having a first supported portion supported by the first supporting portion, the first rod-shaped body having one side and another side opposite to the one side with the first supported portion therebetween, the first rod-shaped body including a measurement unit provided on the one side and a first reservoir provided on the other side, the first reservoir being configured to store a fluid, wherein the first rod-shaped body is balanced horizontally while the first reservoir is filled with the fluid, and wherein, while the first reservoir is not filled with the fluid, the first rod-shaped body is tilted to the one side where the measurement unit is provided, so that the measurement unit is immersed in a solution.

The object and advantages of the present disclosure will be realized and attained by means of the elements and combinations particularly pointed out in the claims.

It is to be understood that both the foregoing general description and the following detailed description are exemplary and explanatory and are not restrictive of the present disclosure.

DETAILED DESCRIPTION

Figure 1:
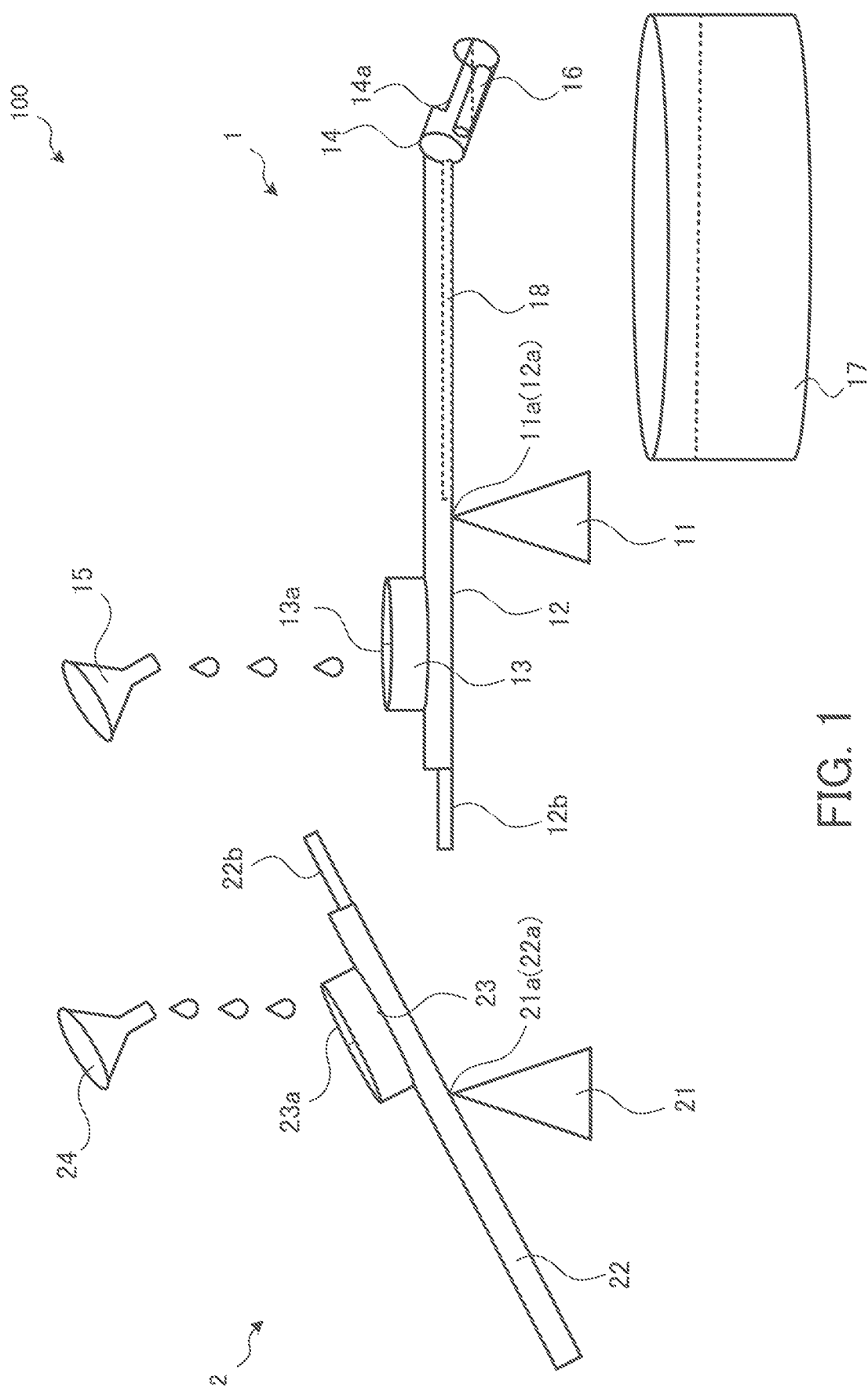
FIG. 1 illustrates a measurement apparatus according to one embodiment.

Hereinafter, a measurement apparatus according to one embodiment will be described in detail with reference to the accompanying drawings.

For easy understanding of the embodiment, the positions, sizes, shapes, ranges, and others of the individual components illustrated in the drawings and the like do not represent the actual positions, sizes, shapes, ranges, and others. Therefore, the embodiment is not limited to the illustrated positions, sizes, shapes, ranges, and others.

Elements that are each expressed in a singular form in the embodiment may be plural in use, expect otherwise particularly specified in writing.

Embodiment

FIG. 1 illustrates a measurement apparatus according to one embodiment.

The measurement apparatus 100 of the present embodiment includes a first mechanical part 1 and a second mechanical part 2.

First Mechanical Part

The first mechanical part 1 includes a base 11 and a rod-shaped body 12.

The base 11 has a top portion 11a that forms a supporting portion (fulcrum), and a supported portion 12a of the rod-shaped body 12 is placed on the supporting portion. In the present embodiment, the base 11 and rod-shaped body 12 are illustrated schematically. How to engage the base 11 and the rod-shaped body 12 with each other is not limited to a particular engagement method, but for example, an engagement method based on a bamboo rocking water fountain mechanism called Shishi-odoshi or a seesaw mechanism may be employed.

A reservoir 13 is provided on one side of the rod-shaped body 12, and an engaged portion 12b is provided at the end on the one side of the rod-shaped body 12. In addition, a sensor mounting portion 14 is provided at the end on the other side of the rod-shaped body 12 opposite to the one side with the supported portion 12a therebetween.

The reservoir 13 has an opening 13a. A liquid (for example, water) discharged from a liquid discharge part 15 flows into the reservoir 13 through the opening 13a. The reservoir 13 stores the liquid flowing therein.

A pH sensor (measurement unit) 16 is mounted in the sensor mounting portion 14. The pH sensor 16 detects the pH of a liquid stored in a water tank 17, for example. The surface of the pH sensor 16 of the embodiment is covered with a glass film. The pH sensor 16 has a short range communication means so as to send information on the detected pH to a computer, not illustrated. Examples of short range communication include Wi-Fi and Bluetooth (registered trademark).

In addition, an opening (cutout) 14a is formed in the sensor mounting portion 14.

A supply pipe 18 is arranged inside the rod-shaped body 12. A cleaning liquid (for example, distillated water) is supplied from a supply means, not illustrated, to the supply pipe 18. The cleaning liquid supplied to the supply pipe 18 is then supplied to the sensor mounting portion 14. The dotted line illustrated in the sensor mounting portion 14 indicates the water level of the cleaning liquid supplied to the sensor mounting portion 14. The cleaning liquid is supplied to the detection part of the pH sensor 16 to thereby clean the detection part of the pH sensor 16.

The water tank 17 is filled with a solution (nutrient solution). For example, crops to be grown in hydroponics are placed in this water tank 17.

The operation of this first mechanical part 1 will be described simply.

Figure 2:
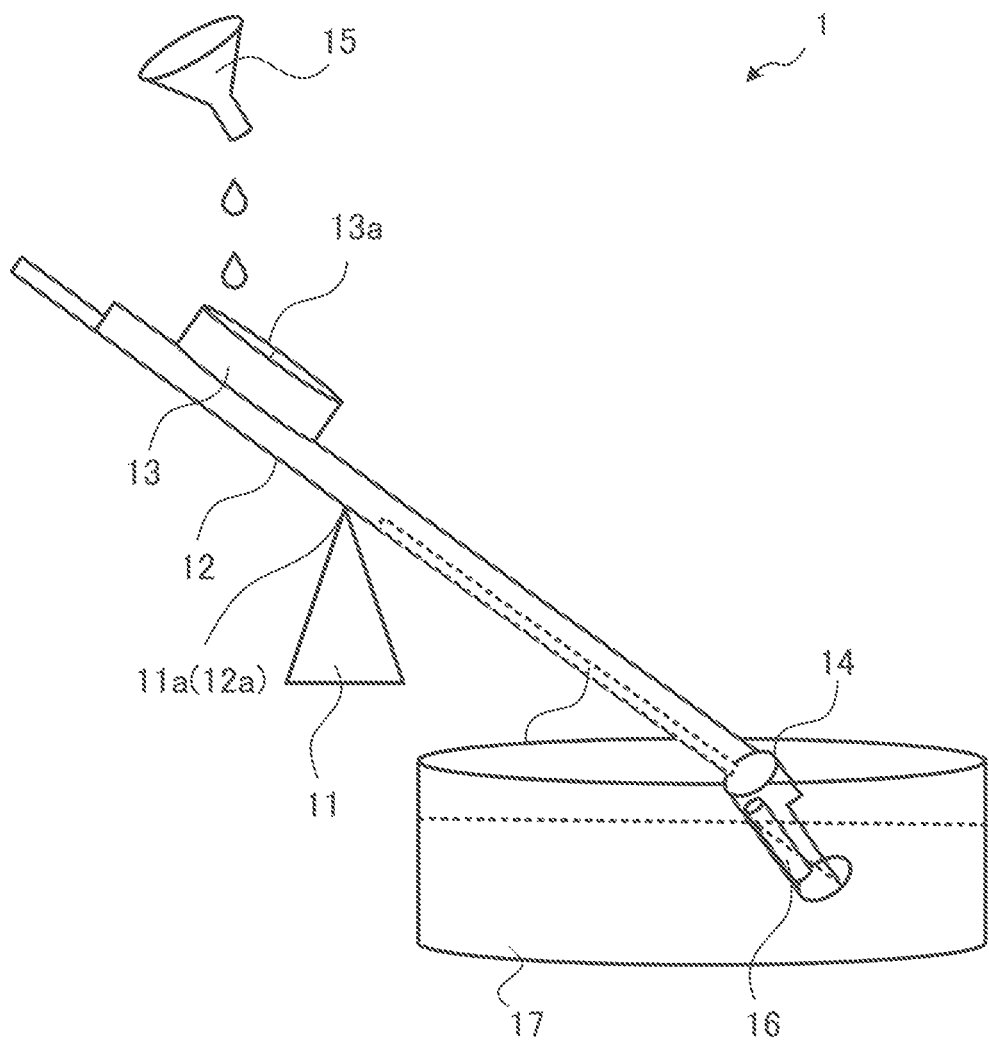
FIG. 2 is a view for describing the operation of a first mechanical part according to the embodiment.

FIG. 2 is a view for describing the operation of the first mechanical part according to the embodiment.

In the following description, the left part of the rod-shaped body 12 from the top portion 11a is referred to as the "left side of the rod-shaped body 12," and the right part of the rod-shaped body 12 is referred to as the "right side of the rod-shaped body 12."

When the reservoir 13 is not filled with a liquid, the right side of the rod-shaped body 12 goes down, so that part or all of the sensor mounting portion 14 is positioned in the water tank 17, as illustrated in FIG. 2. In this state, the solution stored in the water tank 17 flows from the opening 14a into the sensor mounting portion 14, so that the pH sensor 16 is immersed in the solution and is thus able to detect the pH of the solution in the water tank 17. It may be so designed as not to cause the sensor mounting portion 14 to come into contact with the bottom surface of the water tank 17 using the buoyancy of the rod-shaped body 12 and the sensor mounting portion 14. Alternatively, it may be so designed as to cause the sensor mounting portion 14 to come into contact with the bottom surface of the water tank 17 gently using the resistance of the solution in the water tank 17.

As the reservoir 13 becomes filled with the liquid discharged from the liquid discharge part 15, the left side of the rod-shaped body 12 gradually goes down, and accordingly the right side thereof rises. In this connection, as the left side of the rod-shaped body 12 goes down, the position of the opening 13a gradually moves to the left in FIG. 2. Note that the opening 13a is formed large enough to receive the liquid discharged from the liquid discharge part 15. Then, when the reservoir 13 is filled with the liquid, the rod-shaped body 12 is balanced horizontally and remains in equilibrium, as illustrated in FIG. 1. While the liquid continues to be discharged from the liquid discharge part 15, any excess liquid that the reservoir 13 is not able to store spills from the reservoir 13, thereby keeping the rod-shaped body 12 in equilibrium.

It is possible to adjust the period of time during which the pH sensor 16 is placed in the water tank 17, by controlling the amount of the liquid discharged from the liquid discharge part 15 or by changing the capacity of the reservoir 13. In the case where the measurement time of the pH sensor 16 is 5 minutes, for example, the amount of the liquid discharged from the liquid discharge part 15 may be adjusted so as to fill the reservoir 13 with the liquid in 5 minutes.

Second Mechanical Part

Refer now back to FIG. 1. The second mechanical part 2 is configured using the principal of the "bamboo rocking water fountain called Shishi-odoshi."

The second mechanical part 2 includes a base 21 and a rod-shaped body 22.

The base 21 has a top portion 21a that forms a supporting portion (fulcrum), and a supported portion 22a of the rod-shaped body 22 is placed on the supporting portion. In the present embodiment, the base 21 and the rod-shaped body 22 are illustrated schematically. How to engage the base 21 and the rod-shaped body 22 with each other is not limited to a particular engagement method, but for example, an engagement method based on a bamboo rocking water fountain mechanism called Shishi-odoshi or a seesaw mechanism may be employed.

A reservoir 23 is provided on one side of the rod-shaped body 22 away from the top portion 21a, and an engaging portion 22b is provided at the end on the one side of the rod-shaped body 22.

The reservoir 23 has an opening 23a. A liquid (for example, water) discharged from a liquid discharge part 24 flows into the reservoir 23 through the opening 23a. The reservoir 23 stores the liquid flowing therein.

In the following description, the left part of the rod-shaped body 22 from the top portion 21a is referred to as the "left side of the rod-shaped body 22," and the right part of the rod-shaped body 22 is referred to as the "right side of the rod-shaped body 22."

In the second mechanical part 2, when the amount of the liquid stored in the reservoir 23 is less than or equal to a predetermined amount, the left side of the rod-shaped body 22 goes down, and accordingly the right side of the rod-shaped body 22 rises, as illustrated in FIG. 1.

As the reservoir 23 becomes filled with the liquid discharged from the liquid discharge part 24, the right side of the rod-shaped body 22 gradually goes down, and accordingly the left side thereof rises. In this connection, as the right side of the rod-shaped body 22 goes down, the position of the opening 23a gradually moves to the right in FIG. 1. Note that the opening 23a is formed large enough to receive the liquid discharged from the liquid discharge part 24.

The operation of the measurement apparatus 100 will now be described.

As described earlier, when the reservoir 13 is filled with the liquid, the rod-shaped body 12 is balanced horizontally and remains in equilibrium, as illustrated in FIG. 1. While the liquid continues to be discharged from the liquid discharge part 15, any excess liquid that the reservoir 13 is not able to store spills from the reservoir 13, thereby keeping the rod-shaped body 12 in equilibrium. At this time, the cleaning liquid is supplied from a supply means, not illustrated, to the supply pipe 18. The cleaning liquid supplied to the supply pipe 18 is then supplied to the sensor mounting portion 14.

As the reservoir 23 becomes filled with the liquid discharged from the liquid discharge section 24, the right side of the rod-shaped body 22 goes down with the momentum gradually increasing, and accordingly the left side of the rod-shaped body 22 rises.

Figure 3:
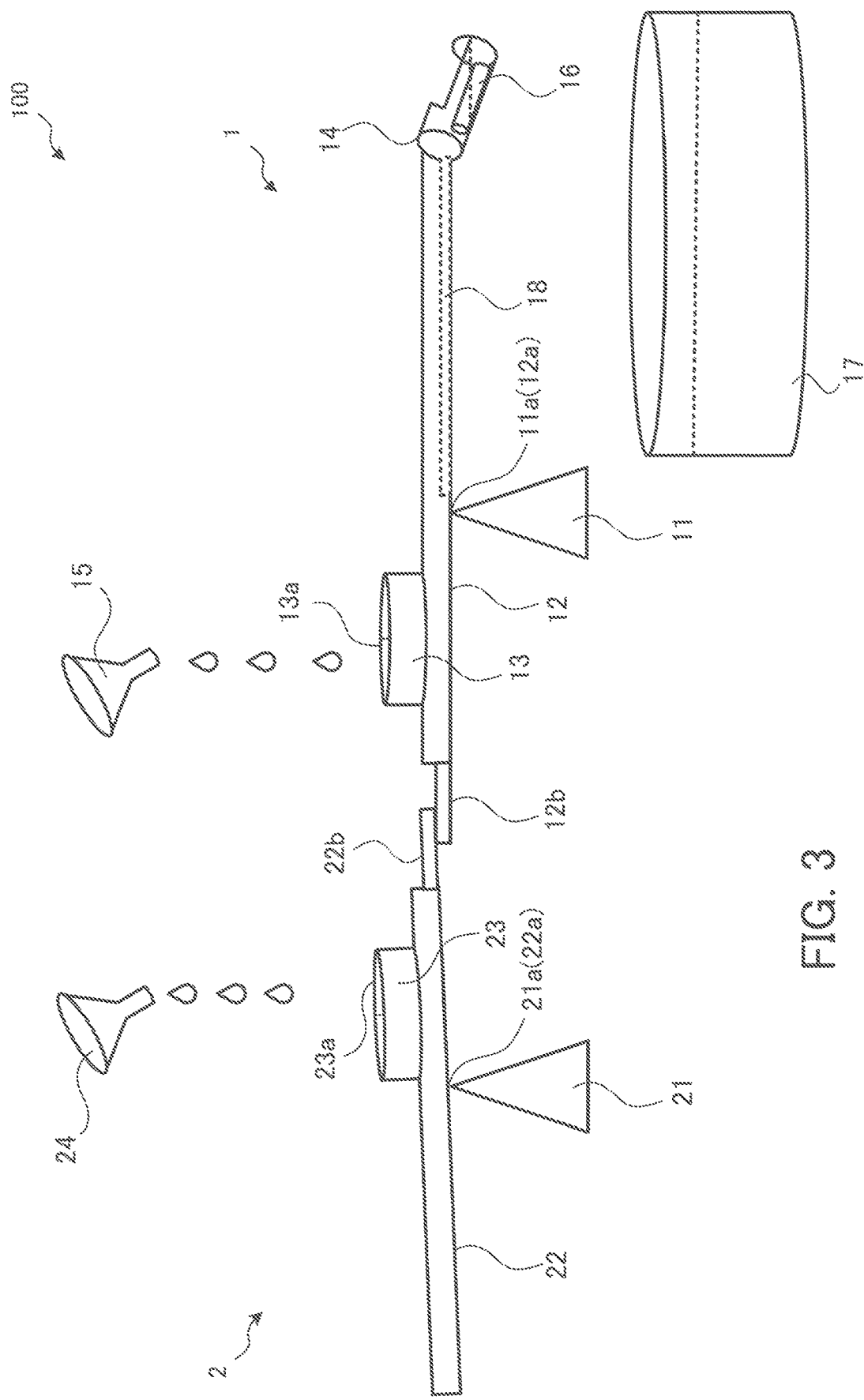
FIGS. 3 to 5 are views for describing the operation of the measurement apparatus according to the embodiment.
Figure 4:
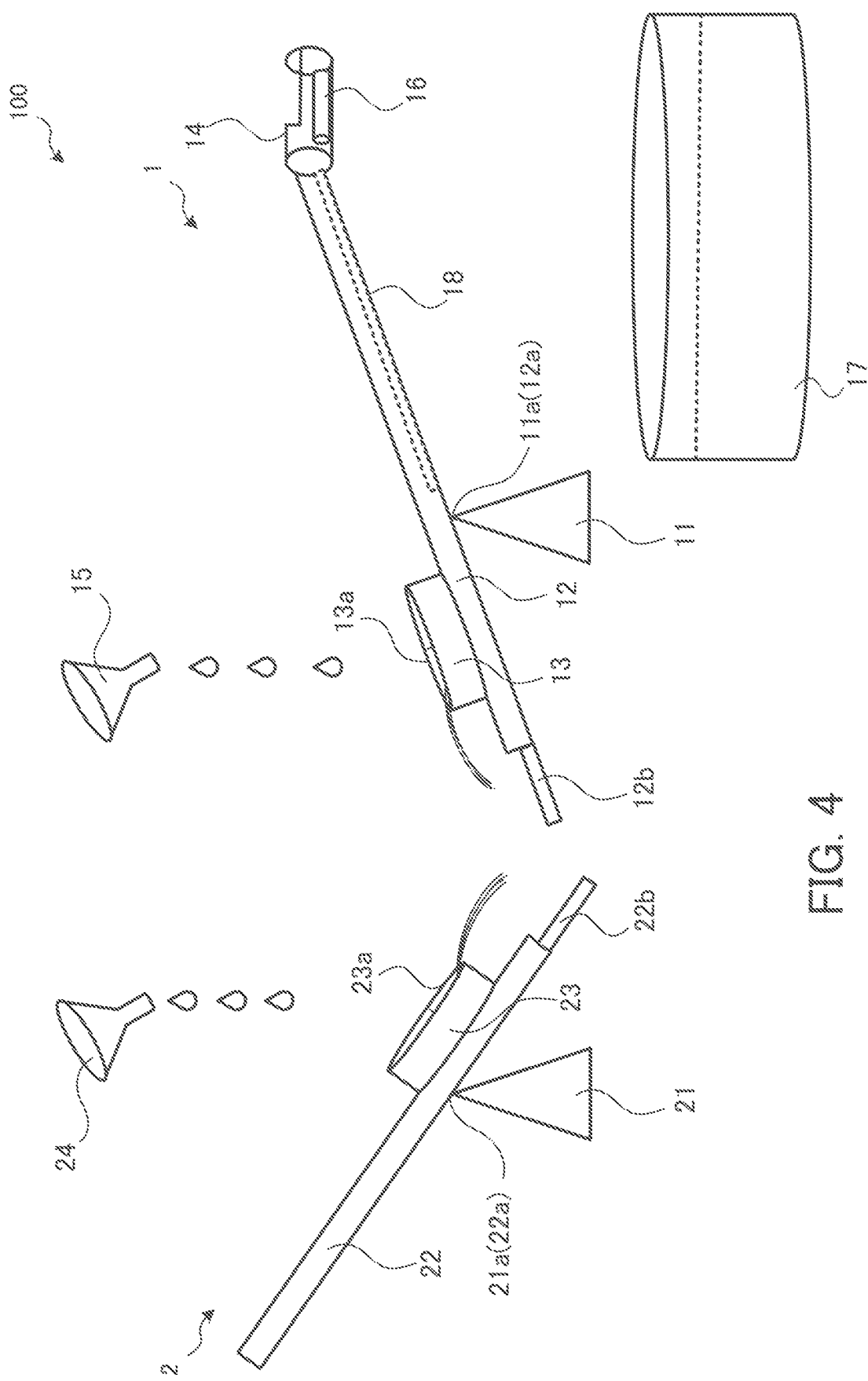
Figure 5:
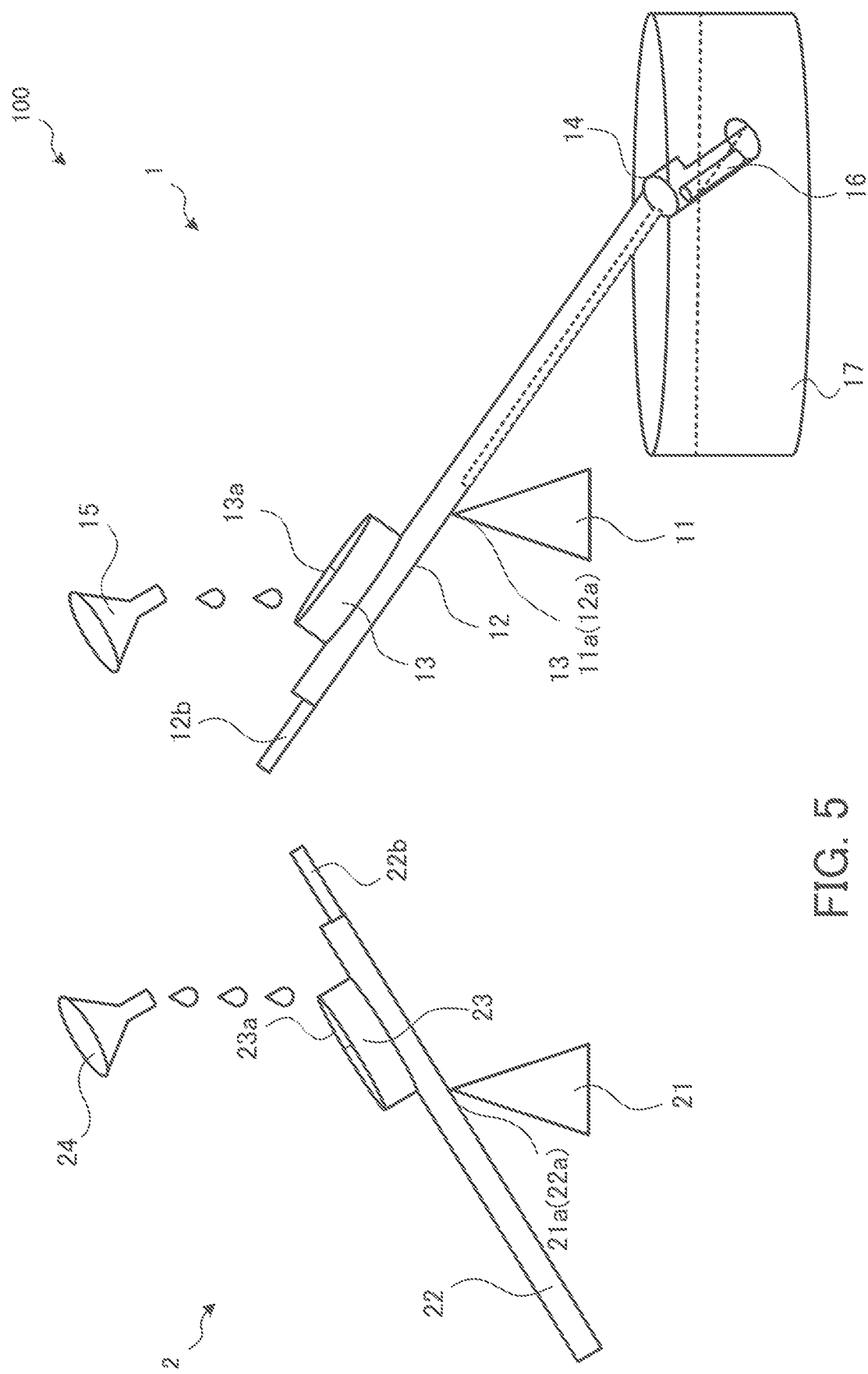

FIGS. 3 to 5 are views for describing the operation of the measurement apparatus according to the embodiment.

As illustrated in FIG. 3, when the right side of the rod-shaped body 22 goes down, the engaging portion 22b bumps into the engaged portion 12b and presses the engaged portion 12b downward in FIG. 3. Then, the left side of the rod-shaped body 12 goes down with great momentum, so that the liquid stored in the reservoir 13 spills from the opening 13a, as illustrated in FIG. 4. As a result, the left side of the rod-shaped body 12 becomes lighter than the right side of the rod-shaped body 12. In addition, after pressing the engaged portion 12b, the right side of the rod-shaped body 22 goes down as well, so that the liquid stored in the reservoir 23 spills from the opening 23a. As a result, the right side of the rod-shaped body 22 becomes lighter than the left side of the rod-shaped body 22. In this connection, it is so designed that the liquid stored in the sensor mounting portion 14 is discharged to the outside through the supply pipe 18 at this time.

After that, the left side of the rod-shaped body 12 rises, and accordingly the right side of the rod-shaped body 12 goes down, as illustrated in FIG. 5. Therefore, the pH sensor 16 is placed in the water tank 17, so that the pH sensor 16 is able to measure the pH of the liquid in the water tank 17. In addition, the right side of the rod-shaped body 22 rises, and accordingly the left side of the rod-shaped body 22 goes down.

After that, the liquid starts to be stored in both the reservoir 13 and the reservoir 23. The flow rates of the liquid discharge parts 15 and 24, the positions of the reservoirs 13 and 23, and other are adjusted so that the reservoir 13 starts to go down before the reservoir 23 starts to go down. With such adjustments, the state is returned back to that illustrated FIG. 1 again.

As described above, the measurement apparatus 100 of the embodiment includes the base 11 with the top portion 11a forming a fulcrum, and the rod-shaped body 12 having the supported portion 12a supported by the top portion 11a and including the pH sensor 16 provided on one side thereof and the reservoir 13 provided on the other side opposite to the one side with the supported portion 12a therebetween. The reservoir 13 is configured to store a liquid. When the reservoir 13 is filled with the liquid, the rod-shaped body 12 is balanced horizontally. When the reservoir 13 is not filled with the liquid, the rod-shaped body 12 is tilted to the side where the pH sensor 16 is provided, so that the pH sensor 16 is immersed in the solution of the water tank 17. With the above configuration, when the measurement by the pH sensor 16 is not performed, the reservoir 13 is filled with the liquid so as to keep the rod-shaped body 12 balanced horizontally. That is, it is possible to prevent dust from sticking to the glass film of the pH sensor 16 due to the pH sensor 16 being left immersed in the water tank 17.

In addition, when the rod-shaped body 12 is tilted to the side where the reservoir 13 is provided, the liquid stored in the reservoir 13 flows out of the reservoir 13, and thus the rod-shaped body 12 is tilted to the side where the pH sensor 16 is provided. This configuration makes it easy to manage the position of the pH sensor 16.

In addition, a power unit (second mechanical part 2 in the embodiment) is provided that tilts the rod-shaped body 12 to the side where the reservoir 13 is provided. By operating the second mechanical part 2 at desired timing, it becomes possible to manage the timing of measurement using the pH sensor 16 easily.

In addition, the supply pipe 18 for allowing the cleaning liquid to pass through is provided inside the rod-shaped body 12 so that the cleaning liquid is supplied to the pH sensor 16 through the supply pipe 18 while the rod-shaped body 12 is balanced horizontally. By doing so, the pH sensor 16 is cleaned.

In addition, the sensor mounting portion 14 is provided that has the opening 14a, allows the pH sensor 16 to be mounted therein, and stores the cleaning liquid to be supplied to the pH sensor 16. Therefore, the sensor mounting portion 14 is able to store the cleaning liquid supplied from the supply pipe 18, which makes it possible to clean the glass film of the pH sensor 16 more reliably. In addition, the cleaning liquid is discharged to the water tank 17 when the measurement using the pH sensor 16 is performed. Therefore, it is easy to replace the cleaning liquid.

In the embodiment, the liquid is stored in the reservoir 13. Alternatively, gas (fluid) that is heavier than air may be stored in the reservoir 13.

Further, in the embodiment, as the power unit that tilts the rod-shaped body 12 to the side where the reservoir 13 is provided, the second mechanical part 2 is used. The power unit is not limited thereto, and for example, a motor is provided in the vicinity of the top portion 11a, and the rod-shaped body 12 may be tilted to the side where the reservoir 13 is provided by rotating the motor. Alternatively, the rod-shaped body 12 may be tilted to the side where the reservoir 13 is provided by using wind power.

Still further, in the embodiment, the pH of the solution (nutrient solution) in the water tank 17 in which crops for the hydroponics are placed is measured. The measurement target is not limited thereto and for example, water-soluble cutting fluids for cutting (for example, soluble type, emulsion type, chemical solution type, and others) may be used.

Heretofore, the measurement apparatus according to the present disclosure has been described with respect to the embodiment illustrated. The configuration is not limited thereto, and the components of each unit may be replaced with other components having equivalent functions. In addition, other desired configurations and steps may be added to the embodiment.

In addition, desired two or more configurations (features) in the above-described embodiment may be combined.

According to one aspect, it is possible to automate measurement in a solution.

All examples and conditional language provided herein are intended for the pedagogical purposes of aiding the reader in understanding the present disclosure and the concepts contributed by the present disclosure to further the art, and are not to be construed as limitations to such specifically recited examples and conditions, nor does the organization of such examples in the specification relate to a showing of the superiority and inferiority of the present disclosure. Although one or more embodiments of the present disclosure have been described in detail, it should be understood that various changes, substitutions, and alterations could be made hereto without departing from the spirit and scope of the present disclosure.

The invention claimed is:

1. A measurement apparatus comprising:
a first base having a first supporting portion forming a first fulcrum; and
a first rod-shaped body having a first supported portion supported by the first supporting portion, the first rod-shaped body having one side and another side opposite to the one side with the first supported portion therebetween, the first rod-shaped body including a measurement unit provided on the one side and a first reservoir provided on the another side, the first reservoir being configured to store a fluid, wherein the first rod-shaped body is balanced horizontally while the first reservoir is filled with the fluid, and wherein, while the first reservoir is not filled with the fluid, the first rod-shaped body is tilted to the one side where the measurement unit is provided, so that the measurement unit is immersed in a solution.

2. The measurement apparatus according to claim 1, wherein, in response to the first rod-shaped body being tilted to the another side where the first reservoir is provided, the fluid stored in the first reservoir flows out of the first reservoir, and then the first rod-shaped body is tilted to the one side where the measurement unit is provided.

3. The measurement apparatus according to claim 1, further comprising a power unit that tilts the first rod-shaped body to the another side where the first reservoir is provided.

4. The measurement apparatus according to claim 3, wherein:

the powering unit includes a second base having a second supporting portion forming a second fulcrum, and a second rod-shaped body having a second supported portion supported by the second supporting portion, the second rod-shaped body having one side and another side opposite to the one side with the second supported portion therebetween, the second rod-shaped body including a second reservoir provided on the one side, the second reservoir being configured to store a fluid;

while an amount of the fluid stored in the second reservoir is less than or equal to a predetermined amount, the second rod-shaped body is tilted to the another side opposite to the one side; and in response to the amount of the fluid stored in the second reservoir being greater than the predetermined amount, a weight of the second rod-shaped body acts on an end portion of the another side of the first rod-shaped body, so as to tilt the first rod-shaped body to the another side where the first reservoir is provided.

5. The measurement apparatus according to claim 1, wherein;

a pipe is provided inside the first rod-shaped body so as to allow a cleaning liquid to pass through the pipe; and the cleaning liquid is supplied to the measurement unit through the pipe while the first rod-shaped body is balanced horizontally.

6. The measurement apparatus according to claim 5, further comprising a container having an opening to place the measurement unit therein, the container being configured to store the cleaning liquid to be supplied to the measurement unit, wherein the cleaning liquid flows from the opening in response to the first rod-shaped body being tilted to the one side where the measurement unit is provided.

* * * * *